United States Patent [19]
Chandler

[11] Patent Number: 5,860,931
[45] Date of Patent: Jan. 19, 1999

[54] ULTRASOUND METHOD AND SYSTEM FOR MEASURING PERFUSION

[75] Inventor: Paul E. Chandler, Santa Cruz, Calif.

[73] Assignee: Acuson Corporation, Mountain View, Calif.

[21] Appl. No.: 949,237

[22] Filed: Oct. 10, 1997

[51] Int. Cl.[6] .................................................. A61B 8/06
[52] U.S. Cl. .......................................................... 600/458
[58] Field of Search .................................. 600/437, 458, 600/443, 504, 505, 526; 424/9.5–9.52

[56] References Cited

U.S. PATENT DOCUMENTS

| | | |
|---|---|---|
| 3,640,271 | 2/1972 | Horton . |
| 4,316,391 | 2/1982 | Tichner .................................. 600/458 |
| 4,712,037 | 12/1987 | Verbeek et al. . |
| 5,040,537 | 8/1991 | Katakura . |
| 5,111,823 | 5/1992 | Cohen . |
| 5,115,809 | 5/1992 | Saitoh et al. . |
| 5,135,000 | 8/1992 | Akselrod et al. . |
| 5,195,520 | 3/1993 | Schlief et al. . |
| 5,197,477 | 3/1993 | Peterson et al. . |
| 5,233,994 | 8/1993 | Shmulewitz . |
| 5,235,984 | 8/1993 | D'Sa . |
| 5,255,683 | 10/1993 | Monaghan . |
| 5,287,753 | 2/1994 | Routh et al. . |
| 5,313,948 | 5/1994 | Murashita et al. . |
| 5,358,466 | 10/1994 | Aida et al. . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |

(List continued on next page.)

FOREIGN PATENT DOCUMENTS

| | | |
|---|---|---|
| 0 357 164 | of 0000 | European Pat. Off. . |
| 0 770 352 A1 | 2/1997 | European Pat. Off. . |

OTHER PUBLICATIONS

"Quantitation of Myocardial Perfusion With Contrast Echocardiography", Sanjiu Kaul, American Journal of Cardiac Imaging, vol. 5, No. 3 (Sep.), 1991, pp. 200–216.

B. Schrope, et al., "Simulated Capillary Blood Flow Measurement Using a Nonlinear Ultrasonic Contrast Agent," Ultrasonic Imaging 14 (1992).

Chandra M. Sehgal, PhD., et al., "Sonographic Enhancement of Renal Cortex by Contrast Media." J. Ultrasound Med, 14; pp. 741–748 (1995)

Chandra M. Sehgal, PhD., et al., "Influence of Postprocessing Curves on Contrast–Echographic Imaging: Preliminary Studies" J. Ultrasound Med, 14; pp. 735–740 (1995).

Chiang C. Mei, et al., "Parametric resonance of a spherical bubble." J. Fluid Mech. (1991) vol. 229.

Deborah J. Rubens, M.D., "Sonoelasticity Imaging of Prostate Cancer: In Vitro Results." Radiology, vol. 195, No. 2, 1995.

(List continued on next page.)

*Primary Examiner*—Francis J. Jaworski
*Attorney, Agent, or Firm*—Brinks Hofer Gilson & Lione

[57] ABSTRACT

An ultrasound method and system for measuring perfusion of a tissue of interest during an ultrasound examination is provided. Perfusion within a region of a tissue can be accurately quantified by measuring a concentration level of contrast agent in a first region before and after reducing the concentration level of contrast agent in a second region. The position of the second region overlaps the position of the first region such that any dimension of the second region differs from any corresponding dimension of the first region by less than a factor of two. With these concentration measurements, contrast agent flow into the first region can be calculated. A corresponding ultrasound image can be created that qualitatively displays perfusion of the tissue.

25 Claims, 6 Drawing Sheets

U.S. PATENT DOCUMENTS

| | | |
|---|---|---|
| 5,425,366 | 6/1995 | Reinhardt et al. . |
| 5,433,204 | 7/1995 | Olson . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,526,816 | 6/1996 | Arditi . |
| 5,540,909 | 7/1996 | Schutt . |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,732,707 | 3/1998 | Widder et al. ............... 600/458 |
| 5,735,281 | 4/1998 | Rafter et al. ................ 600/458 |
| 5,740,807 | 4/1998 | Porter ......................... 600/458 |
| 5,749,364 | 5/1998 | Sliwa, Jr. et al. ........... 600/458 |

OTHER PUBLICATIONS

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Fred Lee, Jr., M.D., "Sonoelasticity Imaging: Results in in Virto Tissue Specimens." Radiology, vol. 181, No. 1 Oct. 1991.

H. Edward Karrer, et al., "A Phased Array Acoustic Imaging System for Medical Use." 1980 Ultrasonics Symposium.

"HP Ultrasound Technologies–Viability." About HP Ultrasound Imaging, WWW document 1997.

J. Ophir, et al., "Elastography: A Quantitative Method for Imaging the Elasticity of Biological Tissues." Ultrasonic Imaging 13, (1991).

J. W. Norris, "The non–linear oscillation of a radially symmetric bubble in a time periodic pressure field." Dynamics and Stability of Systems, vol. 9, No. 1 (1994).

J. A. Hossack, et al., "Improving transducer performance using multiple active layers." SPIE vol. 1733 (1992).

Janet B. Jones–Oliveira, et al., "Transient fluid–solid –solid interaction of submerged spherical shells revisited: Proliferation of frequencies and acoustic radiation effects." Acoustical Society of America, 96(2) Pt. 1, Aug. 1994.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

K.J. Parker, et al., "Tissue Response to Mechanical Vibrations for 'Sonoelasticity Imaging'." Ultrasound in Med. & Biol., vol. 16, No. 3, (1990).

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Kevin J. Parker, PhD, et al., "Sonoelasticity of Organs: Shear Waves Ring a Bell." J. Ultrasound Med. 11 (1992).

Kotaro Sato, et al., "Numerical analysis of a gas bubble near a rigid boundary in an oscillatory pressure field." J. Acoustical Society of America, 95 (5), May 1994.

L.W. Anson et al., "Ultrasonic scattering from spherical shells including viscous and thermal effects." J. Acoustical Society of America, 93 (4), Apr. 1993.

Marc Gensane, "Bubble population measurements with a parametric array." 1994 Acoustical Society of America, 95 (6) Jun.

Michael S. Longuet–Higgins, Resonance in nonlinear oscillations. J. Fluid Mech. (1991) vol. 224.

Michalakis A. Averkiou, et al., "Self–demodulation of amplitude–and frequency–modulated pulses in a thermoviscous fluid." J. Acoustical Society of America, 94 (5), Nov. 1993.

Nico de Jong, "Physical properties and technical aspects of ultrasound contrast agents."

Pi Hsien Chang, et al., "Second Harmonic Imaging and Harmonic Doppler Measurements with Albunex."IEEE Transactions on Ultrasonics, Ferroelectrics, and Frequency Control, vol. 42, No. 6, Nov. 1996.

Robert M. Lerner, et al., "'Sonoelasticity' Images Derived from Ultrasound Signals in Mechanically Vibrated Tissues." Ultrasound in Med. and Biol., vol. 16, No. 3, 1990.

Sharon L. Mulvagh, M.D., et al., "Abstract Session IV Contrast and Ischemia." Journal of the American Society of Echocardiography, vol. 8, No. 3, May 1995.

Samuel Gottlieb, M.D. et al., "Effect of Pressure on Echocardiographic Videodensity from Sonicated Albumin: An In Vitro Model." J. Ultrasound Med. 14 (1995).

"Supplement to Journal of the American College of Cardiology." American College of Cardiology, $45^{th}$Annual Scientific Session, Mar. 24–27, 1996 pp. 21A, 63A, 239–240A.

T.G. Leighton, "Transient excitation of insonated bubbles." Research Notes.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

V.L. Newhouse, et al. "Bubble size measurements using the nonlinear mixing of two frequencies." J. Acoust. Soc. Am. 75 (5), May 1984.

Vokmar Uhlendorf, et al., "Nonlinear Acoustical Response of Coated Microbubbles in Diagnostic Ultrasound." IEEE 1994 Ultrasonics Symposium.

William Armstrong, M.D., et al., "American Society of Echocardiography Position Paper on Contrast Echocardiography." draft 1 –Jun. 6, 1994.

Yang–Sub Lee, et al., "Time–domain modeling of pulsed finite–amplitude sound beams." J. Acoustical Society of America, 97 (2), Feb. 1995.

ULTRASOUND METHOD AND SYSTEM FOR MEASURING PERFUSION

BACKGROUND OF THE INVENTION

Contrast agents can be introduced into a patient to enhance ultrasonic diagnosis, specifically of the vascular system. After injection, the contrast agent travels in the bloodstream from the injection site to an artery. From the artery, the contrast agent infuses into a tissue as blood flows into the capillaries of the tissue. Because contrast agents strongly interact with ultrasonic waves, they return echoes that are clearly distinguished from those returned by blood and tissue. These distinct echoes can be used to measure the rate of perfusion into a tissue to evaluate the viability of blood flow into the tissue.

Currently, qualitative images can be generated by calculating the contrast agent concentration in various mixing volumes as contrast-agent-containing or contrast-agent-free blood flows into or out of a network of mixing volumes. This method is described in Kaul, "Quantification of Myocardial Perfusion with Contrast Echocardiography," American Journal of Cardiac Imaging, Vol. 5, No. 3, Sep. 1991, Pages 200–216. Because a clear mixing volume or a set of mixing volumes within the tissue cannot be adequately defined, only qualitative comparisons can be made of the relative values of perfusion between two or more regions of tissue or between one region of tissue at two or more points in time.

Other methods generate a qualitative image by destroying contrast agents in a tissue over a much larger region than the region that is used to observe reperfusion. Because the destruction region is different from the observation region, blood containing contrast agents travels for some period of time before reaching the observation region. Because different flow patterns of blood carry contrast agents into the observation region at different times, these methods typically produce inaccurate qualitative images.

There is a need, therefore, for an ultrasound method and system for measuring perfusion that overcome the problems described above.

SUMMARY OF THE INVENTION

The present invention is directed to an ultrasound method and system for measuring perfusion. According to a first aspect of this invention, a method for measuring perfusion within a region of a tissue of interest during an ultrasound examination is provided. This method comprises the steps of measuring a concentration level of contrast agent in a first region before and after reducing the concentration level of contrast agent in a second region that overlaps the position of the first region such that any dimension of the second region differs from any corresponding dimension of the first region by less than a factor of two. These concentration measurements are used to calculate contrast agent flow into the first region.

According to a second aspect of this invention, another method for measuring perfusion within a region of a tissue of interest during an ultrasound examination is provided. This method comprises the steps of measuring a concentration level of contrast agent in a second region at equilibrium conditions before and after enhancing a concentration of contrast agent within a first region. The position of the second region overlaps the position of the first region such that any dimension of the second region differs from any corresponding dimension of the first region by less than a factor of two. These concentration measurements are used to calculate contrast agent flow into the second region.

According to a third aspect of this invention, an ultrasound image is generated from contrast agent flow calculated from concentrations of contrast agents from a plurality of regions of a tissue.

According to a fourth aspect of this invention, an ultrasound imaging system is provided to perform the aspects described above.

DETAILED DESCRIPTION OF THE PRESENTLY PREFERRED EMBODIMENTS

Figure 1:
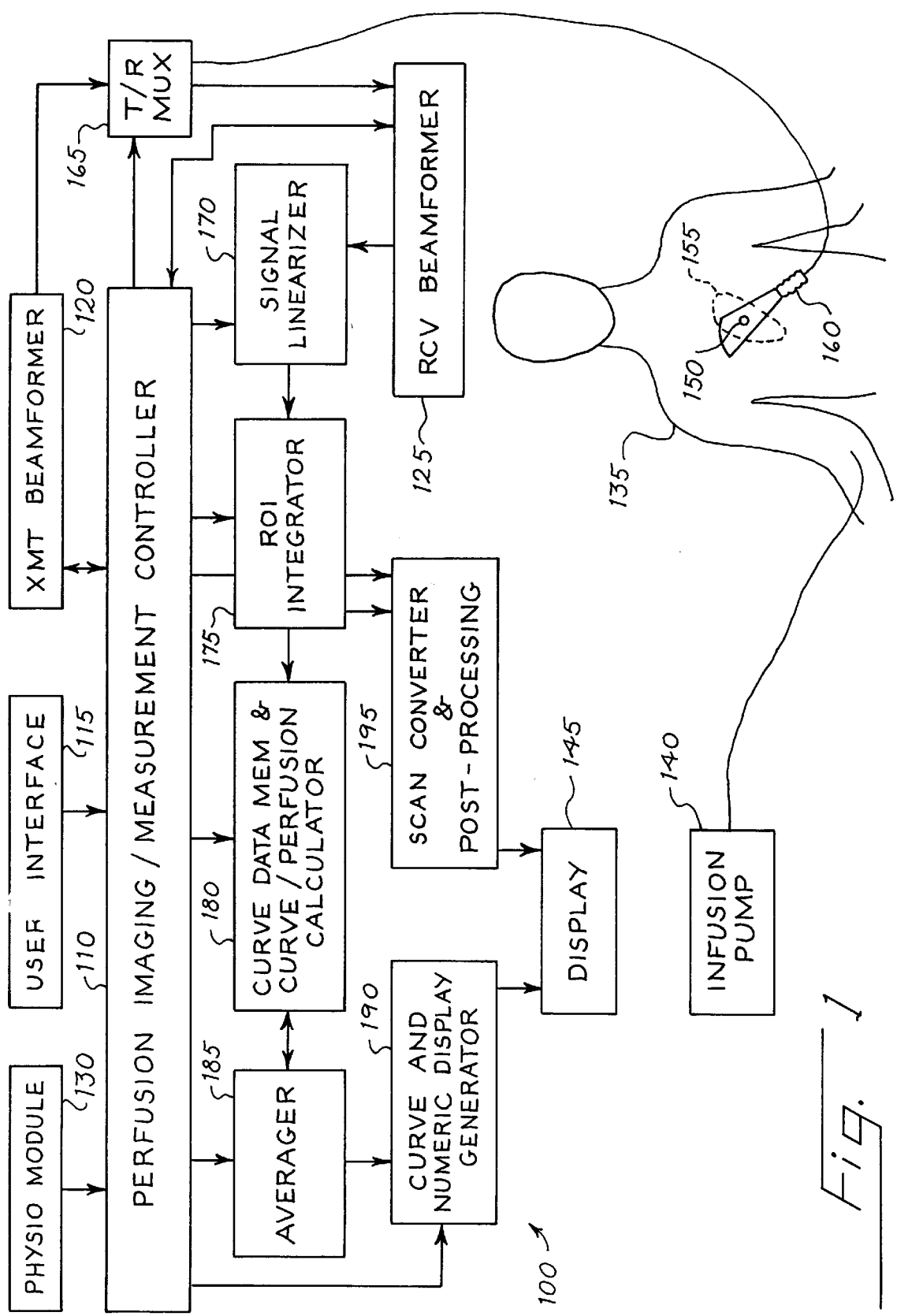
FIG. 1 is a block diagram of an ultrasound system of a preferred embodiment.
Figure 2:
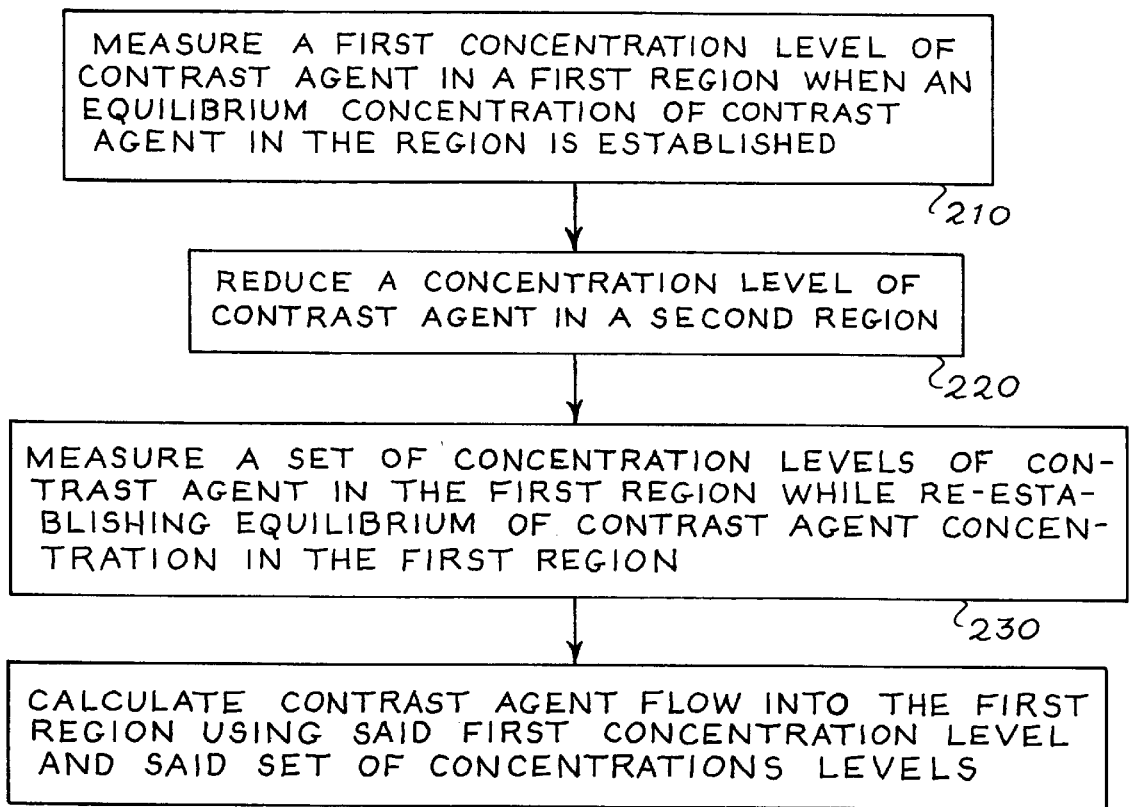
FIG. 2 is a flow chart of a method for measuring absolute perfusion of a tissue of interest during an ultrasound examination of a preferred embodiment.

Turning to the figures, FIG. 2 is a flow chart of a method for measuring perfusion within a region of a tissue of interest during an ultrasound examination. As shown in FIG. 2, this method comprises the steps of measuring a first concentration level of contrast agent in a first region when an equilibrium concentration of contrast agent in the region is established (step 210); then reducing a concentration level of contrast agent in a second region (step 220); then measuring a set of concentration levels of contrast agent in the first region while re-establishing equilibrium of contrast agent concentration in the first region (step 230); and then calculating contrast agent flow into the first region using said first concentration level and said set of concentrations levels (step 240). The steps of this method will be described in more detail below.

Measuring a First Concentration Level of Contrast Agent (Step 210)

As shown in FIG. 2, the first step of the method for measuring perfusion is to measure a first concentration level of contrast agent in a first region when an equilibrium concentration of contrast agent in the region is established (step 210). One way in which to establish equilibrium concentration of contrast agent in the region of interest is to infuse contrast agents into the patient at a constant rate using an infusion pump. The equilibrium concentration is then maintained by the infusion pump for the duration of the study. It is important to note that techniques other than ones using an infusion pump can be used. One such technique uses a single injection of contrast agent designed to have a very long persistence in the body when not destroyed by ultrasound beams so that its half-life exceeds about five minutes.

To measure a first concentration level of contrast agent in the first region, low-powered ultrasound beams are used to prevent significant destruction of contrast agent within the first region. Any form of the ultrasound signal can be used provided that it is directly and linearly correlated to contrast agent concentration. Albrecht has shown that backscattered energy is highly correlated to contrast agent concentration (Albrecht, "Infusion Studies with Levoist in Dogs—A Model for Quantification," Ultrasound Contrast Research Symposium, San Diego, Feb. 7–9, 1997). Methods of measuring backscattered signal intensity are also discussed in U.S. Pat. No. 5,235,984 to D'Sa. While it is preferred that backscatter signal intensity be used to measure contrast agent concentration, other signals can be used. It is preferred that the measurement beams be nearly uniform within the first region.

Signals, such as backscatter signal intensity, corresponding to a plurality of locations in the first region can be summed to generate the first concentration level. For example, the first concentration level can be the sum of a plurality of pixel values corresponding to a plurality of pixel locations in the region of interest. The signals at several locations in the signal path of an ultrasound scanner can be made to be directly and linearly proportional to contrast agent concentrations. Signals can be taken from coherent ultrasound line data to the final detected, scan-converted, and post-processed B-mode image or power Doppler image displayed on a screen or stored in CINE memory. For example, with static objects, complex ultrasound line data can be recorded and complex subtracted before envelope detection and integration, or envelope-detected ultrasound line data can be subtracted before integration. Both may be appropriately prepared for integration and then subtracted after integration. It is also possible to remove any post-processing image filters such as gray scale or color mapping and log compression to linearize image data, such as B-mode or color Doppler energy data.

To achieve stable estimates of perfusion within the first region, it is preferred that additional measurements be acquired and averaged to reduce noisy data. As described below, a user interface on an ultrasound system permits region size to be traded off against the need for longer acquisition times and the averaging of more data. The beamformer can automatically adjust the size of the destructive and measurement beams to match the size of the region.

It is preferred that the first region be symmetrical to ensure consistent results regardless of region orientation. For example, in a region that is long in one dimension and thin in the other two, a wave of perfusion will be observed propagating in the direction of the blood flow if the long dimension of the region is oriented parallel to the blood flow. In contrast, if a short dimension of the rectangular volume is oriented perpendicular to the blood flow, contrast agent will perfuse into the region in a nearly step-function-like manner as the contrast agent rapidly flows into the region along the thin dimension. That is, when a symmetrically shaped region of interest is used, the measurement will not depend on the direction from which contrast agent enters the region of interest.

Reducing a Concentration Level of Agent in a Second Region (Step 220)

The second step of the method for measuring perfusion is to reduce a concentration level of contrast agent in a second region of the tissue (step 220). Unlike prior methods of measuring perfusion, the position of the second region (i.e., the reduction region) overlaps the position of the first region (i.e., the measurement region) such that any dimension of the second region differs from any corresponding dimension of the first region by less than a factor of two. Preferably, any dimension of the second region differs from any corresponding dimension of the first region by less than a factor of 1.5. More preferably, the two regions completely overlap so that no contrast agent outside the first region that may enter the first region during reperfusion is destroyed. With this overlap, accurate quantitative measurements of perfusion can be made, as will be described in more detail below, even if different flow patterns of blood carry contrast agents into the measurement region at different times.

Figure 3A:
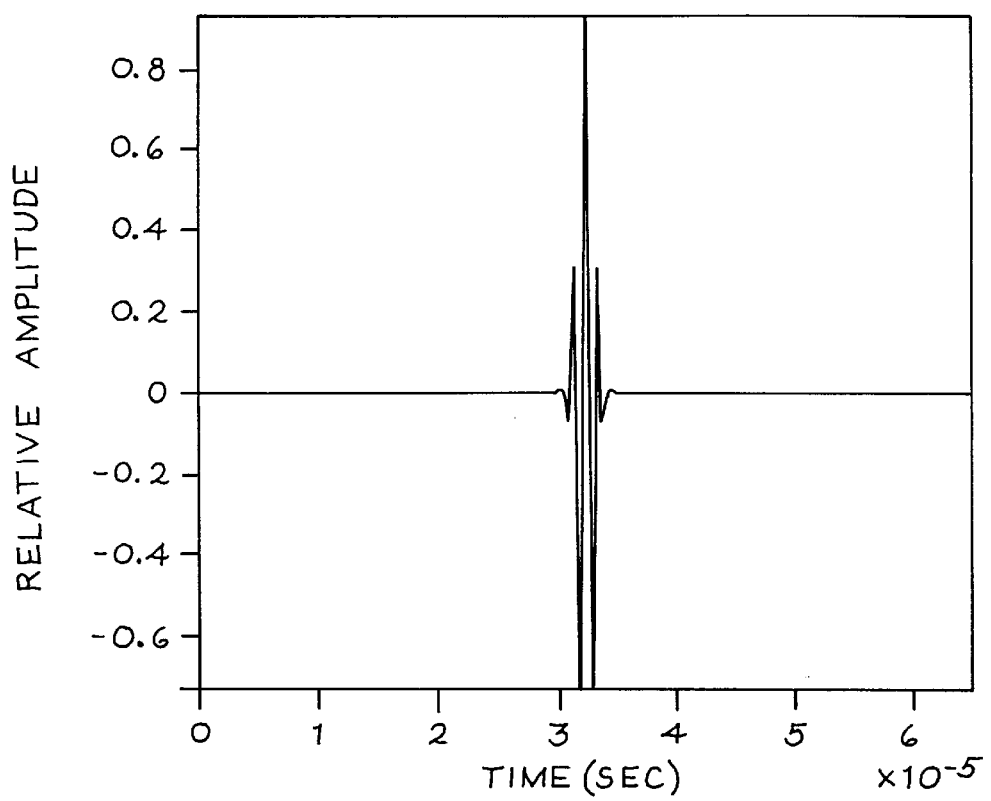
FIG. 3A is a graph of the time domain transmitted pulse shape used to calculate curves for FIGS. 3B–D.
Figure 3B:
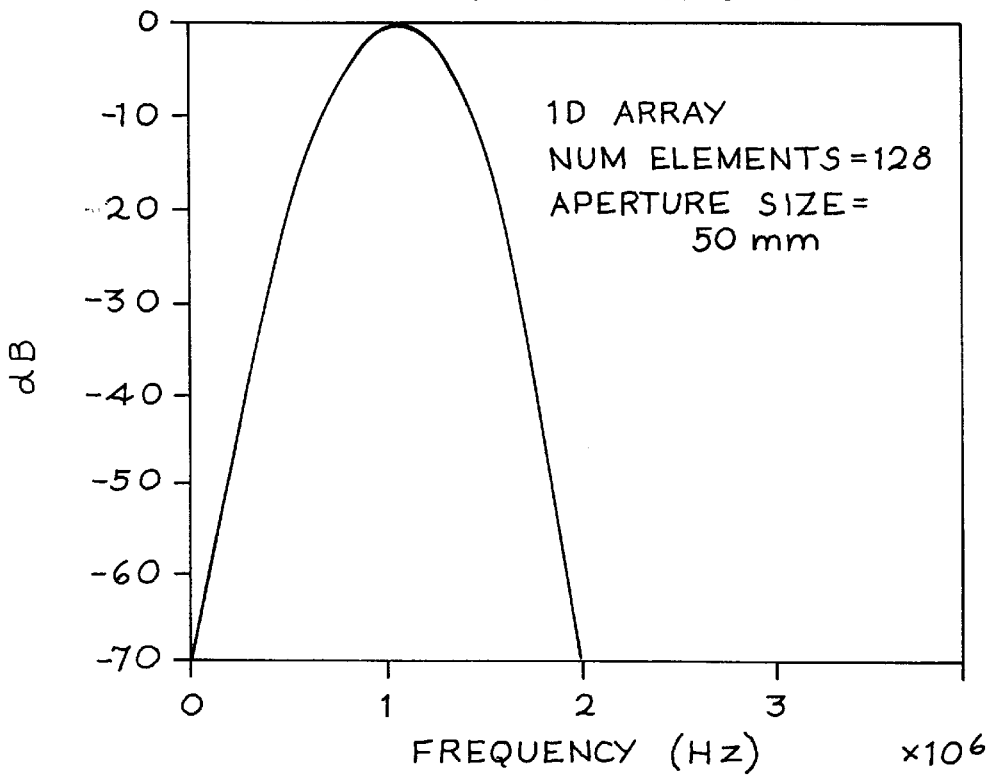
FIG. 3B is a graph of the spectrum of the pulse in FIG. 3A.
Figure 3C:
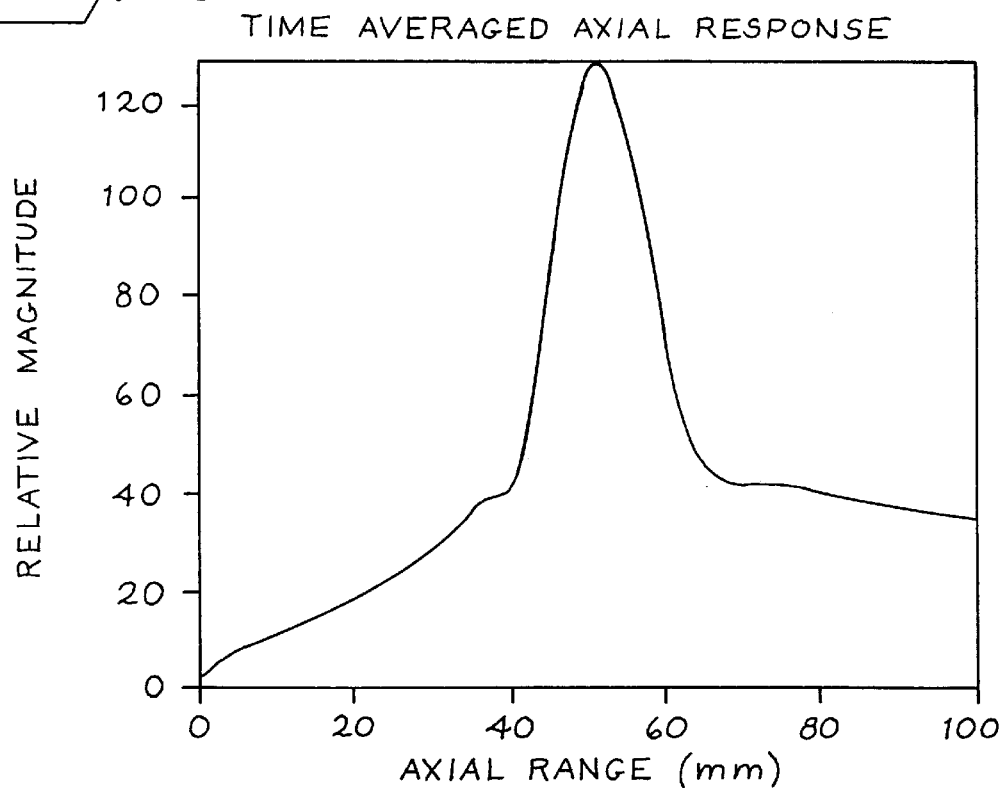
FIG. 3C is a graph of a relative amplitude of the time average axial response of an ultrasonic beam with an F number of one.
Figure 3D:
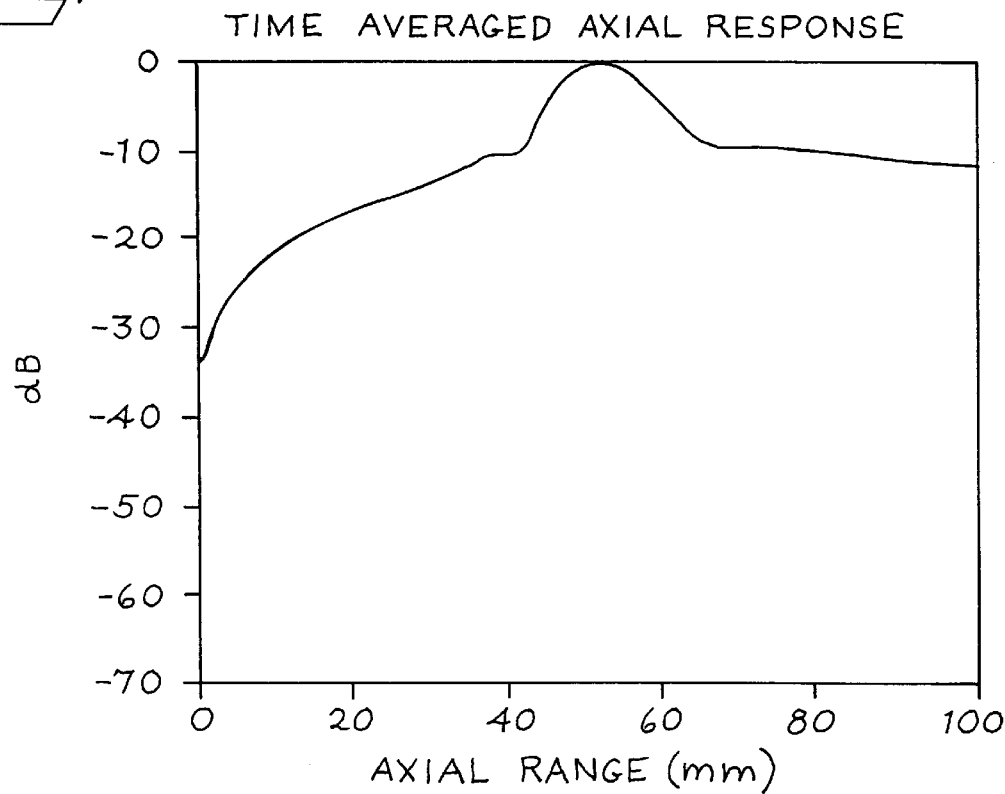
FIG. 3D is a graph of a time average axial response in dB of an ultrasonic beam with an F number of one.
Figure 4A:
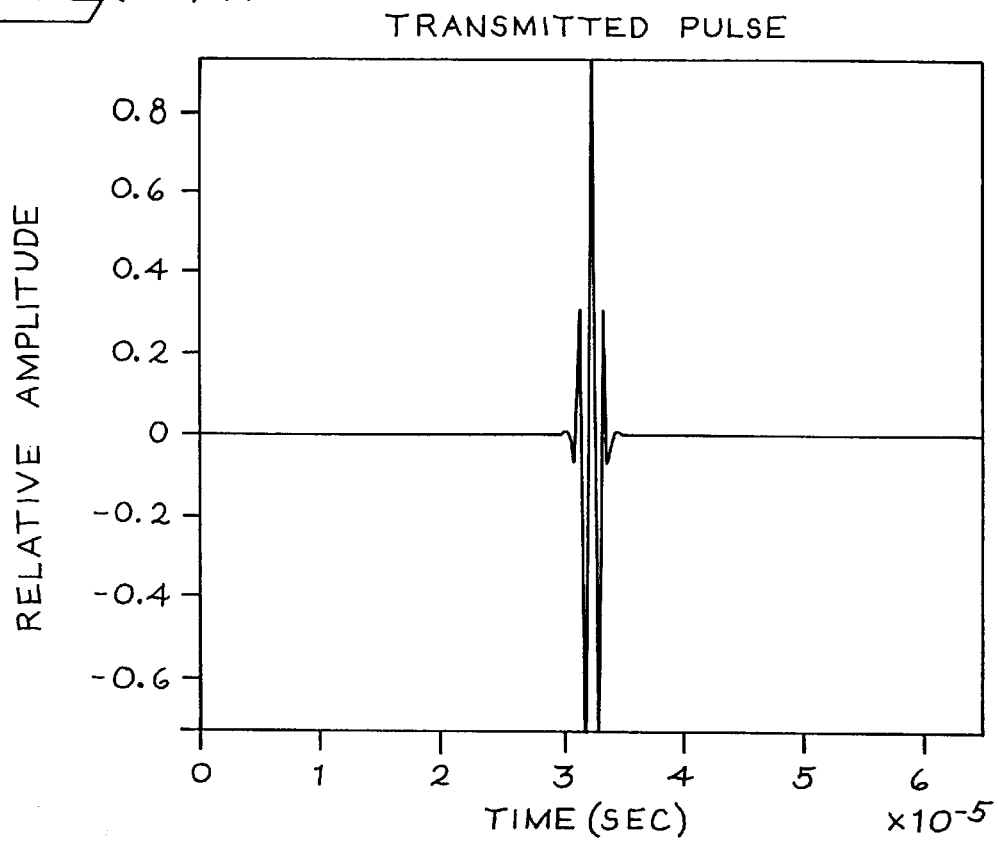
FIG. 4A is a graph of the difference frequency pulse shape of the mixed time domain transmitted pulses used to calculate curves for FIGS. 4B–D.
Figure 4B:
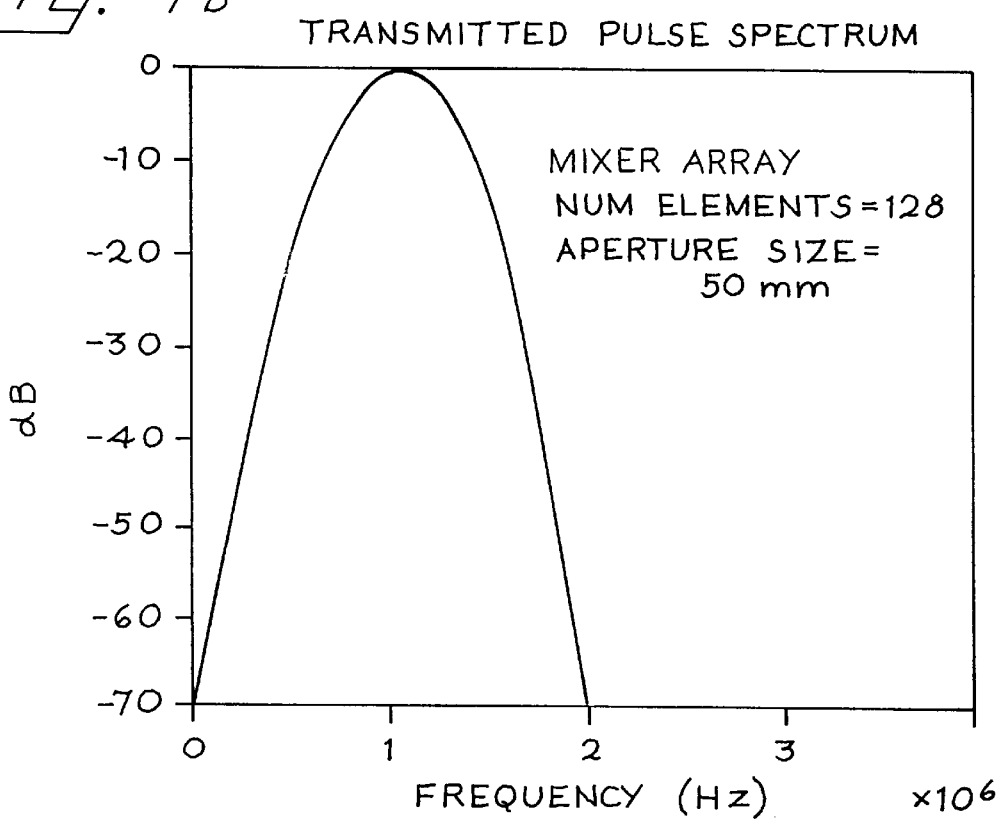
FIG. 4B is a graph of the spectrum of the pulse in FIG. 4A.
Figure 4C:
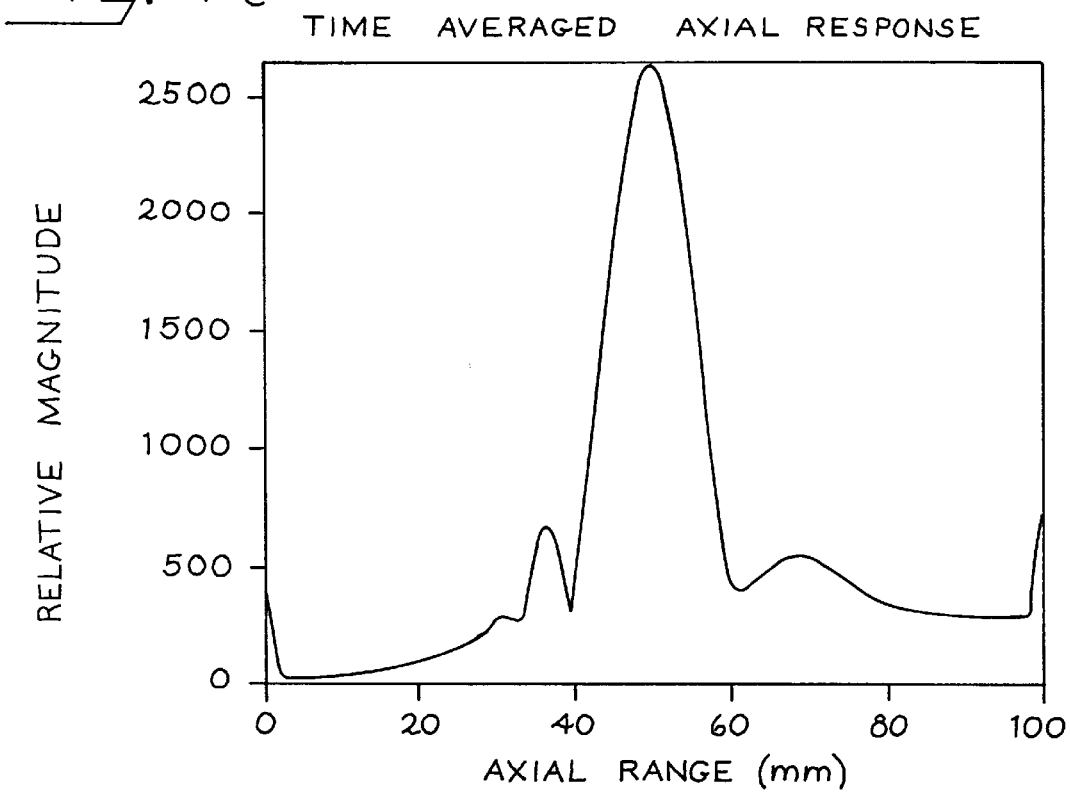
FIG. 4C is a graph of a relative amplitude of the time average axial response of an ultrasonic beam with an F number of one split in two halves about its center, each half driven at a different center frequency.
Figure 4D:
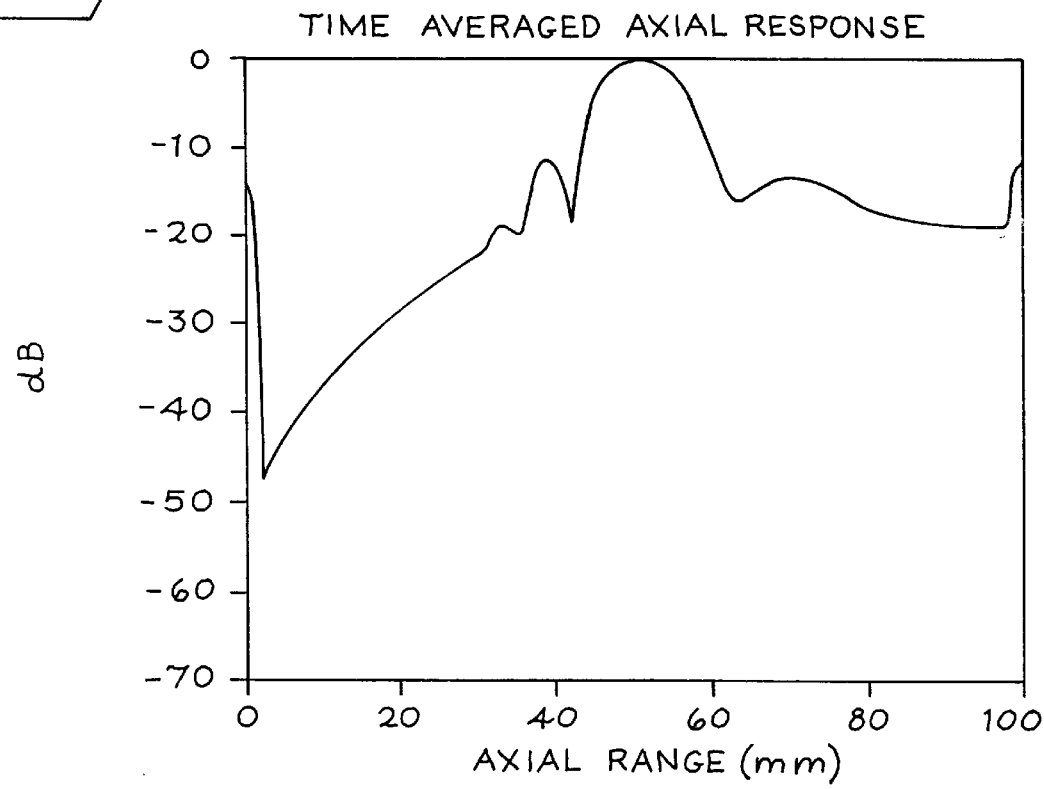
FIG. 4D is a graph of a time average axial response in dB of an ultrasonic beam with an F number of one split in two halves about its center, each half driven at a different center frequency.

Contrast agent destruction can be confined within the second region by controlling the distribution of acoustic energy deposition in the elevation and azimuthal directions, as is well understood in the art. This includes use of single or small groups of ultrasound lines fired in azimuth, electronic beam control of an azimuthal aperture, geometric focusing of an elevation aperture using a lens, and electronic beamforming in both the azimuthal and elevation dimensions using a two-dimensional array. One way to control deposition of energy to a confined region in range is through use of low F number (i.e., focal range divided by aperture width) beams that have very high degrees of focus. It is preferred that beams with an F number less than about five (more preferably an F number of about one) be used. FIGS. 3A–3D are graphs of the time domain transmitted pulse shape, the transmitted pulse spectrum, the relative amplitude of the time average axial response, and the time average axial response in dB, respectively, of an ultrasound beam having an F number of one. As can be seen in FIG. 3D, 10 dB more energy is delivered at the beam's focal region than outside the focal region.

An improvement on this method uses a beam with an F number of one that is split in two halves about its center. FIGS. 4A–4D are graphs of this beam's difference frequency time domain transmitted pulse shape, transmitted pulse spectrum, relative amplitude of the time average axial response, and time average axial response in dB. Not shown in these figures is that one half of the beam is driven at a low frequency, the other half is driven at a high frequency, and both halves are focused at the same focal point. The two beams have their greatest overlap at this focus and combine to give sum and difference frequencies. By selecting either the sum or difference frequency to be at the resonance of the contrast agent, contrast agent destruction can be enhanced near the focus.

Another way to use sum or difference frequencies to localize destruction within the second region is by using a first transducer array transmitting energy having a spectrum of low frequencies and a second transducer array transmitting energy having a spectrum of high frequencies. The specific frequencies are chosen such that the sum or difference frequency spectrum formed during the mixing of the first and second transmit spectra approximates the resonance spectrum of the contrast agent. First and second transducer arrays can be separately-held transducers (e.g., single-element or array transducers), or they can be portions of the same array transducer. For example, first and second transducer arrays can comprise opposing halves of a one-dimensional array transducer, inner and outer groups of annuli from an annular array transducer, inner and outer regions of a two-dimensional array transducer, or opposing halves or quadrant pairs of a two-dimensional array transducer. In this context, a two-dimensional array can be approximated by an array having fewer elements in one dimension than in the other dimension.

In operation, the imaging array can be used to both fire destructive beams at the low frequency and to conduct imaging for measurements with low transmit energy beams. The second high frequency transducer array can be pointed at the region by the user and controlled, as the first transducer array, by the scanner. The user can finely adjust contrast agent destruction to occur within the region by adjusting beam intensity until the acoustic intensity is above the contrast agent destruction threshold level within the region, transitions rapidly at the boundary of the region, and is below the contrast agent destruction threshold level outside the region.

Mixing of two signals, which produces sum and difference frequencies, can be used more effectively to control the destruction of contrast agent. Mixing of pulses having bandlimited spectra combine to produce pulses having sum and difference frequencies. The resonant spectrum of the contrast agent is measured. This spectrum depends on the physical properties of the contrast agents, their environment, and their size distribution. Measurement of resonance spectra is well known and understood in the art. The spectra are selected such that either their sum spectrum or their difference spectrum will match the resonance spectrum of the contrast agent. Since contrast agent expansion and contraction in response to the interrogating acoustic field is much greater when the interrogating field is chosen to be at the resonance frequency for the contrast agent, the contrast agent is more easily destroyed when driven at its resonant frequency. Consistently, a population of contrast agents having a resonance spectrum is more likely to be destroyed when interrogating with a pulse having a spectrum matching the resonance spectrum of the contrast agent population. Thus, by using the methods here, and split beams or separate beams with bandlimited spectra having greatly different center frequencies and having significant overlap only at the overlapping foci for each beam, more mixed beam energy is localized near the focus than is achievable with more conventional single spectrum transmit means and, therefore, contrast agent destruction is better confined near the focus with the mixing method.

Figure 5:
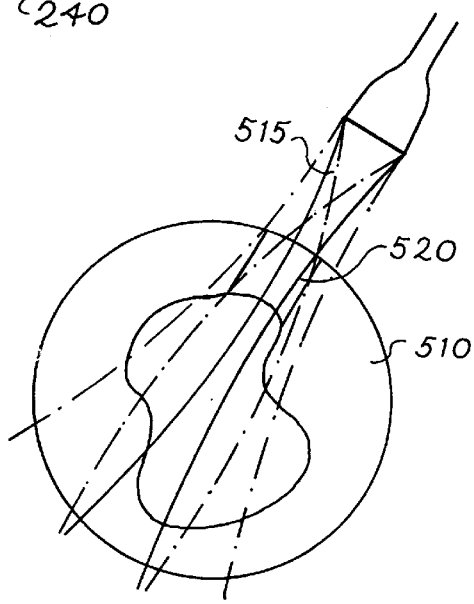
FIG. 5 is an illustration of how anatomical boundaries can be used to limit reduction in contrast agent reduction along a beam axis.

Anatomical boundaries may also be used to limit destruction along the beam axis. To limit destruction in range, the destructive beam can be oriented to cross nearly perpendicularly to an anatomical boundary, as illustrated in FIG. 5. FIG. 5 shows a short axis view of a heart 510 with an ultrasound beam 515 intersecting the heart wall at nearly normal incidence. Since blood cannot enter the region of interest 520 through endocardial or epicardial boundaries, it does not matter if contrast agents are destroyed outside these boundaries. Azimuthal and elevation control can be easily implemented, as described above, to provide a well-defined contrast-agent destruction region within which to conduct the perfusion measurements.

It is preferred that the concentration of contrast agents in the second region be reduced to about zero to avoid complications due to non-uniform contrast agent destruction. If contrast agents are not uniformly destroyed within the second region, adjustments may be necessary to the flow model described below. For the purposes of this detailed description, it is assumed that uniform or complete destruction of contrast agents within the second region can be achieved.

Because the destructive beam intensity does not immediately rise and fall, there may be misalignment between the first and second regions. Viewing the reduction on a display, a user can adjust the transmit gain until the rapid rise and fall of beam intensity near the transmit focus rise above contrast agent destruction threshold as the beam enters the regions and fall below bubble destruction threshold as it exits the regions. In this way, a user can observe the second region and increase or decrease the constant gain on the destructive beam until the regions match. The gain adjustment may be done manually by the operator via a destructive beam transmit gain control while observing an ultrasound image or could be performed by the system. The system would integrate backscatter over two regions, one being inside the first region and the other being a portion of the image outside the first region. It will then adjust the gain until the integral of one region stops changing and before the other starts to change. This balance point occurs when the region of destruction matches the first and second regions. Alternatively, the system or user can adjust the size and shape of the first region until it matches the visible region of destruction defining the second region.

Measuring a Set of Concentration Levels during Reperfusion (Step 230)

The third step is to measure a set of concentration levels of contrast agent in the first region while re-establishing equilibrium of contrast agent concentration in the first region (step 230). After contrast agent is reduced in the first region, blood will carry additional contrast agents into the first region to reestablish equilibrium. The method of measuring performed in this step is similar to the method described above in reference to step 210. It is preferred that the number of concentration levels measured in the set of concentration levels be sufficient to permit the calculation described in step 240 below before equilibrium concentration is reestablished. The timing of the measurements following the destructive beam can be regularly, irregularly, or randomly spaced in time.

Calculating Contrast Agent Flow Per Volume of Tissue (Step 240)

The fourth step is to calculate contrast agent flow into the first region using said first concentration level and said set of concentrations levels (step 240). If fresh blood entering the tissue instantly and thoroughly mixes within the tissue, contrast agent concentration within the tissue will rise exponentially, as will the measurement of the linearized signal measured within the first region. With this assumption, reperfusion can be modeled mathematically as described in the paragraph below. It is important to note that this assumption does not limit the invention and that blood flow can be calculated after measuring a blood transfer function h(t,f,V).

Figure 6:
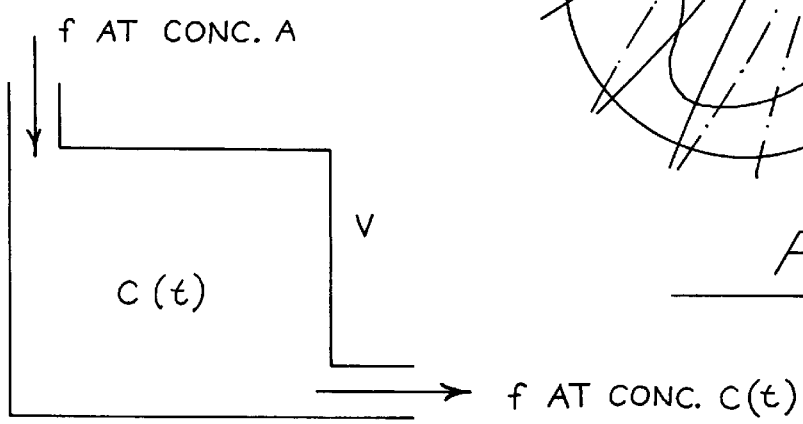
FIG. 6 illustrates a model showing perfusion in a tissue of interest.

Let perfusion in the tissue be modeled as in FIG. 6, where fresh blood containing contrast agent at a constant contrast agent concentration A enters the tissue at a constant flow rate f and where the tissue has a tissue volume V and a contrast concentration C(t) at time t. As mentioned above, all blood entering V is assumed to be instantly and completely mixed with the rest of the blood in V. Conservation of mass requires that blood leave V at the same rate f at which fresh blood enters V. The blood leaving V at time t will carry contrast agent away at concentration C(t). The rate of change of contrast agent within V is defined by:

$$\frac{dC(t)}{dt} = \frac{fA}{V} - \frac{C(t)f}{V},$$

which can be solved to show that $$\ln[A - C(t)] = \ln[A - C(0)] - (f/V)t.$$

Therefore, a plot of 1 n[A–C(t)] will have slope–

$$-(f/V).$$

The slope, therefore, gives a quantitative value that represents the contrast agent flow per volume of tissue within the first region.

Therefore, [A–C(t)] can be calculated by subtracting each measurement C(t) made at times t following a destructive beam sequence from the measurement A made under conditions where the tissue in the first region was fully perfused with blood containing contrast agent at concentration A. (Of course, because A is really an exponential, it never truly reaches equilibrium in a mathematical sense. In a practical sense, A reaches equilibrium due to random variations in concentrations and, eventually, to quantum effect.) Note the further benefit that [A–C(t)] is automatically adjusted by having all tissue contributions removed, since each measurement is really [A +tissue] or [C(t) +tissue] to give [A +tissue]–[C(t)+tissue]=[A–C(t)].

It is important to note that it is not necessary that the concentration of contrast agent be reduced to zero during the destructive beam sequence. Any post-reduction concentration is sufficient as long as the concentration is sufficiently below A to permit accurate measurement of the slope of 1 n[A–C(t)]. It is preferred that measurements be repeated and averaged to acquire a more statistically significant data set, especially in a noisy environment. System gain is not important to the calculation as long as it remains constant throughout the study.

In the equations above, it was assumed that blood occupies all of V. If blood is instead confined to a fractional volume P, blood would be confined to blood volume PV, and the calculations would be modified accordingly to be $$\ln[AP - C(t)] = \ln[AP - C(0)] - (f/VP)t.$$

Therefore, a plot of 1n[AP–C(t)] that will have slope–

$$-(f/VP),$$

,which is a measure of the contrast agent flow per volume of blood within V.

P can be calculated through a relatively simple procedure. Let $C_v(t)$ =the concentration of contrast in a large vessel, such as the left ventricle, aorta, or hepatic artery. Let $C_T(t)$=the concentration of contrast agent in tissue. Both $C_v(t)$ and $C_T(t)$ will contain signals from blood or tissue when measured over the region of interest. Tissue signals can be assessed immediately following an extensive destruction sequence long enough and strong enough to ensure that all contrast in the tissue within the region of interest has been reduced to negligible levels. It may be desirable to increase the size of the destructive beam to exceed the dimensions of the measurement region of interest during this measurement to better ensure the absence of contrast in the tissue of interest during measurement. Destruction of all contrast in blood will be more difficult due to the high velocity of blood flow in the vessels large enough to conduct the $C_v(t)$ measurements.

One effective alternative method to compensate for backscatter from blood is to turn down the system gain to a level known from pre-contrast experiments to be sufficiently low to ensure that $C_v(t)$ =when no contrast is present. It is preferred that measurements made to determine P be made with gain set to this level. Gain can be returned to any desired level once P is known. Under these conditions, $C_v(0)$ =0; $C_v(\infty)$=A; $C_T(0)$=measurement of tissue backscatter; and $C_T(\infty)$=measurement of tissue backscatter+AP . P can be calculated as $$P = \frac{(C_T(\infty) - C_T(0))}{(C_v(\infty) - C_v(0))}, \text{ or } P = \frac{(C_T(\infty) - C_T(0))}{(C_v(\infty))}\bigg|_{lowgain}$$

It is preferred to measure $C_v$ and $C_T$ under identical conditions. This can be done by choosing nearly identical acoustic propagation paths to the measurement region to avoid variations in gain arising from different attenuation and other beam aberration effects along the two different paths. In all other measurements, the paths are identical, and this problem does not exist.

Flow in body tissues can only be approximated by the assumption that blood flowing into the volume instantly and thoroughly mixes within the volume. It is possible to define a blood transfer function, h(t, f, VP) defining the blood flow through a tissue volume V having blood volume VP when blood flows into the tissue at constant flow rate f Transfer functions are well known in the art of linear systems theory, and as defined here, h(t, f, VP) represents the measurement of contrast concentration leaving V when an impulsive contrast agent concentration is injected at t=0 into the flow stream as it moves into V at constant flow rate f. Although more complex, it is also possible to determine similar functions when f and VP vary with time. A new differential equation can be written to solve for flow once h(t, f, VP) is known. It is always desirable to approximate h(t, f, VP), as we did in our example with the assumption that blood flowing into the volume instantly and thoroughly mixes within the volume, to permit definition of a differential equation that is easy to solve, providing a means to determine a flow parameter. With the assumption of our example, we had indirectly assumed that h(t, f, VP) was of the form:

$$h(t,f,VP) = \frac{1}{\lambda} e^{-\lambda t}$$

where, $$\lambda = (f/VP)$$

Turning again to the figures, FIG. I is a block diagram of an ultrasound system 100 that can be used with the methods described above. A perfusion imaging/measurement controller I 10 accepts region of interest placement information from the operator via user interface 115 and then determines the number of destructive beams and measurement transmit beams that must be fired to cover the region of interest along with the focal position and beam pattern parameters for each beam. This information is passed onto the transmit beamformer 120 and is used to configure the transmit beamformer 120 for scanning. Similarly, the perfusion imaging/measurement controller 110 determines the number of receive beams and all receive beam pattern parameters for the receive beams. This information is passed onto a receive beamformer 125 and used to configure the receive beamformer 125 for scanning. Once scanning has begun, the operator is able to adjust transmit beam gain for the destructive transmit beam via a gain adjustment available through the user interface 115. A physio module 130 provides ECG and/or respiration signals that may be used by the perfusion imaging/measurement controller 110 to control timing of scans.

When ready to perform a study, the operator injects contrast agents into the patient 135 using an infusion pump 140, for example, and waits until an equilibrium concentration of contrast agents is established in the patient's blood. The increase to equilibrium is observed by watching the contrast image and by monitoring the concentration measurement value reported on a display 145. Once equilibrium concentration has been established, the operator, via the user interface 115, positions and sizes a measurement region of interest 150 over a desired tissue of interest 155, and then instructs the system 100 to begin transmitting destructive beams into the region of interest 150. While observing the destruction on an ultrasound image provided on the display 145, the operator adjusts destructive beam gain until the region of destruction matches the measurement region of interest.

Once the region of destruction has been adjusted, the operator instructs the system 100 to begin perfusion measurement via the user interface 115. While conducting perfusion measurements, the perfusion imaging/measurement controller 110 arranges to make concentration measurements at equilibrium just before contrast agent destruction, to reduce the concentration level of contrast agents in the destruction region, to conduct a series of measurements of concentrations following contrast agent destruction in the measurement region, and to repeat the entire sequence many times to average the results. During this process, the perfusion imaging/measurement controller 110 controls access to and from the transducer 160 using a transmit/receive multiplexer 165. Measurement signals received by the receive beamformer 125 are sent to a signal linearizer 170, which converts the received signals into a signal that is directly and linearly proportional to backscattered signal energy. The linearized signal is sent to a region of interest integrator 175, which selects data from within the region of interest and sums each linearized value within the region of interest. Region of interest integral values are then sent to the curve data memory and curve/perfusion calculator 180 along with time stamps to indicate where they were made in the measure at equilibrium, reduce, and measure concentration set sequence. A curve data memory and curve/perfusion calculator 180 both store the data and perform the perfusion calculations by the methods described above. Averaging of values from subsequent acquisition cycles may preferably be done on the raw data before perfusion estimation, or on the perfusion measurements following estimation or any other reasonable grouping of the data sets. This is done in the averager 185. Averaged values are sent to a curve and numeric display generator 190, where averaged curves for the data from the acquisition sequences and numeric perfusion display information are generated and sent to the display 145.

An alternate signal path through a scan converter and post-processing unit 195 permits the perfusion data to be presented as an image on the display 145. Scanning to prepare data for an image is very different from scanning to conduct perfusion measurements and the two cannot be run simultaneously other than in an interleaved mode. To simplify this discussion we will assume that they are run at different times. When acquiring an image, the perfusion imaging/measurement controller 110 instructs the transmit beamformer 120 to destroy contrast agents everywhere within a perfusion box selected by the user via user interface 115. It then instructs the transmit beamformer 120, transmit/receive multiplexer 165 and receive beamformer 125 to interrogate many system determined overlapping small regions of interest that cover the perfusion box. Acquisition sequences proceed as before with the exception that destruction is over the perfusion box and that concentration is now simultaneously measured in all system generated regions of interest within the perfusion box. The data for each region of interest is linearized and integrated as before in the signal linearizer 170 and the region of interest integrator 175 before being sent to the scan converter and post-processing unit 195, where it is converted into an image and sent to the display 145.

There are several alternatives to the above preferred embodiments. In one alternative embodiment, contrast activation is used instead of contrast destruction. Activatable contrast agents are discussed in U.S. Pat. No. 5,040,537 to Katakura and in U.S. patent application Ser. No. 08/916,163, hereby incorporated by reference, which is assigned to the assignee of the present invention. Instead of reducing the concentration of contrast agents, this method enhances the concentration of contrast agents and measures a set of concentration levels as equilibrium is established. The rate of change of contrast agent within V is defined by:

$$\frac{dC(t)}{dt} = -\frac{C(t)f}{V},$$

which can be solved to show that $$\ln[C(t)] = \ln[b] - (f/V)t.$$

Similar to the measurement of equilibrium concentrations measured for the destroyable contrast agents, equilibrium concentrations must be measured for activatable contrast agents as well. These measurements will include contributions from previously activated and long lasting contrast agents now circulating freely within the patient's blood and now at equilibrium, any low level scattering produced by the contrast agent before activation, and tissue contributions. Unlike with the destroyable contrast agents, equilibrium concentrations, D(infinity) must be subtracted from the series of contrast measurements, C(t), when activatable contrast agents are used, such that ln[C(t)−D(infinity)] has slope−(f/V). Therefore, a plot of ln [C(t)] will have slope−(f/V), and a concentration level at equilibrium need not be measured.

In another alternative embodiment, a related perfusion image can be created that, though not quantitative, can be used by an operator to identify regions of reduced perfusion that may require further quantitative perfusion assessment by the methods described above. The related qualitative image can be produced as follows. First, expand the destruction region of interest to cover a larger area of the reference image in which the perfusion measurements are being made. The destruction region may be expanded to be as large as the reference image. Next, perform the perfusion assessment on many small and possibly overlapping measurement regions of interest placed within the destruction region and convert the measured value of flow for each measurement region of interest into an image through application of a gray-scale, color, or combined gray-scale and color post-processing map, for example. Note that the acquisition times for these images are typically long and that these images are potentially noisy. Temporal persistence can be used to average the images to reduce the presence of noise.

Tissue may move throughout the acquisition sequence. It may, therefore, be necessary to track the tissue to permit proper positioning of the destruction and measurement regions (i.e., the second and first regions) over the tissue of interest at its correct position at the correct time to ensure that optimal perfusion estimates can be made. Estimation of tissue expansion/contraction, translation, and rotation can be calculated using auto-correlation methods well known in the art. Tracking moving tissue is described in U.S. patent application Ser. No. 08/916,358, which is assigned to the assignee of the present invention. Tracking permits knowledge of the position of the tissue of interest surface at all times allowing the regions to be stretched, compressed, rotated, or repositioned to match the tissue at the required times. Region tracking is a complex and computationally intensive task. Approximations will be made to permit practical implementation. One such approximation is to conduct tracking only within the two-dimensional image plane even though it is known that this motion is three-dimensional. This approximation may require the operator to carefully select the image scan plane to keep the moving region within the scan plane where it can be properly tracked. Additionally, measurements can be made at a fixed point in a cyclic motion of the tissue, such as at a fixed point in the cardiac cycle or respiration cycle. Such an embodiment is described in U.S. patent application Ser. No. 08/948,815, hereby incorporated by reference, which is assigned to the assignee of the present invention.

In another alternative, more than one simultaneous region of interest is used. In this situation, the user interface would allow the user to select a plurality of regions, and the ultrasound system would be modified to allow the measurement and destruction beams to be directed to more than one region of interest. Flow from one region to another region would be limited to a level that would insignificantly affect the measurement. It is preferred that each region of interest would be spaced far apart from another region of interest to ensure that blood leaving one region does not flow into another region.

As used above, operative contrast agent signifies contrast agent that is effective to return an enhanced echo signal, either at the fundamental or the harmonic frequency. Disrupted contrast agent signifies contrast agent that has been destroyed or otherwise modified such that it returns a substantially reduced or negligible echo signal. Also as used herein, a set of ultrasound signals includes signals associated with one or more transmit events that create a region of disrupted contrast agent or region of activate contrast agent or that provide an image or measurement of a selected region of the tissue.

It is intended that the foregoing detailed description be understood as an illustration of selected forms that the invention can take and not as a definition of the invention. It is only the following claims, including all equivalents, that are intended to define the scope of this invention.

What is claimed is:

1. A method for measuring perfusion within a region of a tissue of interest during an ultrasound examination comprising the steps of:
   (a) measuring a first concentration level of contrast agent in a first region when an equilibrium concentration of contrast agent in the region is established; then
   (b) reducing a concentration level of contrast agent in a second region, a position of the second region overlapping a position of the first region such that any dimension of the second region differs from any corresponding dimension of the first region by less than a factor of two; then
   (c) measuring a set of concentration levels of contrast agent in the first region while re-establishing equilibrium of contrast agent concentration in the first region; and then
   (d) calculating contrast agent flow into the first region using said first concentration level and said set of concentrations levels.

2. The method of claim 1, wherein the position of the second region overlaps the position of the first region such that any dimension of the second region differs from any corresponding dimension of the first region by less than a factor of 1.5.

3. The method of claim 1, wherein said first and second regions are symmetrical.

4. The method of claim 1, wherein an equilibrium concentration of contrast agent in the first region is established by infusing contrast agents at a constant rate using an infusion pump.

5. The method of claim 1, wherein concentration levels are measured in steps (a) and (c) using an ultrasound signal that is linearly correlated to contrast agent concentration.

6. The method of claim 1, wherein concentration levels are measured in steps (a) and (c) by measuring backscattered signal intensity.

7. The method of claim 1, wherein the concentration level of contrast agent in the second region is reduced in step (b) to about zero.

8. The method of claim 1, wherein the concentration level of contrast agent in the second region is reduced in step (b) by using an ultrasonic signal characterized by a ratio of focal range to aperture width of less than about 5.

9. The method of claim 1, wherein the concentration level of contrast agent in the second region is reduced in step (b) by using an ultrasonic signal characterized by a ratio of focal range to aperture of about 1.

10. The method of claim 1, wherein the concentration level of contrast agent in the second region is reduced in step (b) by using a first transducer array to deliver energy at a first frequency and a second transducer array to deliver energy at a second frequency, a sum or difference of said first and second frequencies approximating a resonance spectrum of the contrast agent.

11. The method of claim 10, wherein the first and second transducer arrays are selected from a group consisting of separate portions of an array transducer, opposing halves of a one-dimensional array transducer, inner and outer groups of annuli from an annular array transducer, inner and outer regions of a two-dimensional array transducer, opposing halves of a two-dimensional array transducer, and opposing quadrant pairs of a two-dimensional array transducer.

12. The method of claim 1, wherein anatomical boundaries are used to limit destruction of contrast agent outside the first region in at least one of its dimensions.

13. The method of claim 1 further comprising the step of tracking a moving tissue of interest and wherein steps (b) and (c) are performed in response to said moving tissue of interest being at a selected location.

14. The method of claim 1, wherein contrast agent flow into the first region is calculated in step (d) by calculating a slope of $1 n[A—C(t)]$, wherein A comprises said first concentration level of contrast agent and C(t) comprises a concentration level of said set of concentration levels.

15. The method of claim 1, wherein contrast agent flow into the region is calculated in step (d) by:
   (d1) calculating a slope of $ln[AP-C(t)]$, wherein A comprises said first concentration level of contrast agent, P comprises a fractional blood volume of the tissue, and C(t) comprises a concentration level of said set of concentration levels; and then
   (d2) multiplying said slope calculated in step (d1) with the fractional blood volume of the tissue.

16. The method of claim 15, wherein the fractional blood volume of the tissue is calculated by $$P = \frac{(C_T(\infty) - C_T(0))}{(C_v(\infty) - C_v(0))},$$

wherein $C_v(t)$ comprises a concentration of contrast agent in a large blood vessel and $C_T(t)$ comprises a concentration level in the tissue.

17. The method of claim 1, wherein a plurality of first regions and a plurality of second regions are used.

18. A method for measuring perfusion within a region of a tissue of interest during an ultrasound examination comprising the steps of:
(a) measuring a first concentration level of contrast agent in a first region when an equilibrium concentration of contrast agent in the region is established; then
(b) enhancing a concentration level of contrast agent in a first region; then
(c) measuring a set of concentration levels of contrast agent in a second region while establishing equilibrium of contrast agent concentration in the first region, a position of the second region overlapping a position of the first region such that any dimension of the second region differs from any corresponding dimension of the first region by less than a factor of two; and then
(d) calculating contrast agent flow into the first region using said first concentration level and said set of concentrations levels.

19. The method of claim 18, wherein contrast agent flow into the first region is calculated in step (d) by
(d1) calculating a slope of $\ln[C(t)-D(\text{infinity})]$, wherein $C(t)$ comprises a concentration level of said set of concentration levels and $D(\text{infinity})$ comprises a measure of equilibrium concentration; and then
(d2) multiplying said slope calculated in step (c1) with a fractional blood volume of the tissue.

20. The method of claim 18, wherein the position of the second region overlaps the position of the first region such that any dimension of the second region differs from any corresponding dimension of the first region by less than a factor of 1.5.

21. The method of claim 18, wherein said first and second regions are symmetrical.

22. A method for creating an ultrasound image using measured perfusion of a tissue of interest comprising the steps of:
(a) measuring a plurality of first concentration levels of contrast agent in a respective plurality of regions of the tissue when an equilibrium concentration of contrast agent in the regions is established; then
(b) reducing a concentration level of contrast agent in said plurality of regions; then
(c) measuring a set of contrast agent concentrations for a plurality of said plurality of regions while re-establishing equilibrium of contrast agent concentration in said plurality of regions; then
(d) calculating contrast agent flow into said plurality of regions using said plurality of first concentration levels and said set of contrast agent concentrations; and then
(e) creating an ultrasound image using said contrast agent flow.

23. A method for creating an ultrasound image using measured perfusion of a tissue of interest comprising the steps of:
(a) measuring a first concentration level of contrast agent in a first region when an equilibrium concentration of contrast agent in the region is established; then
(b) enhancing a concentration level of contrast agent in a plurality of regions of the tissue; then
(c) measuring a set of contrast agent concentrations for a plurality of said plurality of regions while establishing equilibrium of contrast agent concentration in said plurality of regions; then
(d) calculating contrast agent flow into said plurality of regions using said first concentration level and said set of contrast agent concentrations; and then
(e) creating an ultrasound image using contrast agent flow.

24. In an ultrasound imaging system comprising a transmit/receive beamformer system operative to generate transmit waveforms and responsive to ultrasonic signals radiated by an image region, said beamformer system characterized by beamformer parameters; a display responsive to the beamformer system and operative to generate at least one image on the display, the improvement comprising:
means, responsive to the transmit/receive beamformer system, for measuring a first concentration level of contrast agent in a first region;
means, responsive to the transmit/receive beamformer system, for reducing a concentration level of contrast agent in a second region, a position of the second region overlapping a position of the first region such that any dimension of the second region differs from any corresponding dimension of the first by less than a factor of two; and
means, responsive to the transmit/receive beamformer system, for calculating contrast agent flow into the first region using said first concentration level and said set of concentrations levels.

25. The invention of claim 24, further comprising means, responsive to the transmit/receive beamformer system, for creating an ultrasound image using calculated contrast agent flow.

* * * * *

UNITED STATES PATENT AND TRADEMARK OFFICE
CERTIFICATE OF CORRECTION

PATENT NO.   : 5,860,931
DATED         : January 19, 1999
INVENTOR(S) : Paul E. Chandler It is certified that error appears in the above-identified patent and that said Letters Patent is hereby corrected as shown below:

Title page,

Column 1,
Line 6, under "OTHER PUBLICATIONS", delete "Virto" and substitute -- Vitro -- in its place.
Line 20, under "OTHER PUBLICATIONS", delete "-solid" (second occurrence).

Column 2,
Line 16, after "nonlinear" insert -- bubble --.

Specification

Column 7,
Line 10, delete "slope-" and substitute -- slope -- in its place.
Line 45, delete "slope-" and substitute -- slope -- in its place.
Line 49, delete ",which" and substitute -- which -- in its place.

Column 8,
Line 4, delete "=when" and substitute -- = 0 when -- in its place.
Line 27, delete "rate f" and substitute -- rate f. -- in its place.
Line 53, delete "I 10" and substitute -- 110 -- in its place.

UNITED STATES PATENT AND TRADEMARK OFFICE
CERTIFICATE OF CORRECTION

PATENT NO. : 5,860,931
DATED : January 19, 1999
INVENTOR(S) : Paul E. Chandler

It is certified that error appears in the above-identified patent and that said Letters Patent is hereby corrected as shown below:

Column 10,
Line 44, delete "plot of In" and substitute -- plot of 1n -- in its place.

Claim 19,
Line 7, delete "(cl)" and substitute -- (d1) -- in its place.

Signed and Sealed this

Twenty-third Day of October, 2001

Attest:

*Nicholas P. Godici*

NICHOLAS P. GODICI
*Acting Director of the United States Patent and Trademark Office*

*Attesting Officer*